United States Patent [19]

Lamprecht

[11] 4,003,795
[45] Jan. 18, 1977

[54] PROCESS FOR THE DETERMINATION OF AT LEAST ONE OF THE ISOENZYMES OF LACTATENDEHYDROGENASE

[75] Inventor: Walther Lamprecht, Iserhagen FB, Germany

[73] Assignee: Kommanditgesellschaft Schwarzhaupt, Cologne, Germany

[22] Filed: Sept. 12, 1975

[21] Appl. No.: 612,633

[30] Foreign Application Priority Data

Sept. 12, 1974 Germany .......................... 2443741

[52] U.S. Cl. ........................................ 195/103.5 R
[51] Int. Cl.$^2$ ........................................ G01N 31/14
[58] Field of Search ...................... 195/103.5 R, 99

[56] References Cited
UNITED STATES PATENTS

| | | |
|---|---|---|
| 3,663,374 | 5/1972 | Moyer et al. ............... 195/103.5 R |
| 3,713,986 | 1/1973 | Bergmeyer et al. ........ 195/103.5 R |
| 3,862,010 | 1/1975 | Rush et al. ................. 195/103.5 R |
| 3,867,258 | 2/1975 | Forgione ................... 195/103.5 R |

*Primary Examiner*—A. Louis Monacell
*Assistant Examiner*—C. A. Fan
*Attorney, Agent, or Firm*—Michael J. Striker

[57] ABSTRACT

Process for the determination of at least one of the isoenzymes of lactatedehydrogenase by visually observing and recording the conversion of lactate and nicotinamideadenine-dinucleotide to pyruvate wherein said conversion is carried out at a buffer specific pH value of 6–6.5. The invention also encompasses test reagents for use in making such determinations and also diagnostic aids containing the same for use in detecting abnormal changes in the female genital tract and diagnostic methods utilizing such aids.

6 Claims, No Drawings

PROCESS FOR THE DETERMINATION OF AT LEAST ONE OF THE ISOENZYMES OF LACTATENDEHYDROGENASE

This invention relates to a process for the determination of one or more or all of the isoenzymes of lactatedehydrogenase (LDH) by means of the conversion of lactate and nicotinamide-adenino-dinucleotide (NAD$^+$) to pyruvate which conversion is observed as a color change.

It is known that lactatedehydrogenase, conventionally known as LDH exists in five iso forms. The activity and presence of the individual isoenzymes are dependent on the use of different substrates and pH optima. These, however, are not completely known for the individual isoenzymes.

In order to determine the totality of the isoenzymes, one has heretofore either separated the isoenzymes electrophoretically (for instance as described in "Die Isoenzyme der Lactatdehydrogenase," G. Thieme Verlag, Stuttgart 1972, page 29) or the total LDH contained in a test solution, bound as LDH-2 to 5 and/or to the frequently occurring LDH-1 determined. A general review of the presently available working methods for such determinations is to be found for example in the book "Enzymatische Analyse", vol. 1, Verlag Chemie, Weinheim 1970, page 557. According to that work there is disclosed for the transformation of lactate to pyruvate a pH optimum of 8.3 and 8.9. Actually there has heretofore been used for all of the described determination methods, a basic or at the least an about neutral pH value in order to detect as completely as possible the isoenzymes.

From Lamprecht et al (Cardiology 56: 371-375 (1971/72) and Fortschritte der klinischen Chemie, Enzyme und Hormone, Verlag der Wiener medizinischen Akademie 1972 (pages 272-283) it has been determined that single isoenzymes through variations in pH are converted one into the other and also that a conformation change takes place.

It is an object of this invention to eliminate the inaccuracies and complicated working procedures associated with the known methods for isoenzyme determinations.

It is another object to provide a process for an optimal determination of the whole or the totality of the LDH isoenzyme and especially the isoenzymes 4 and/or 5 and still further of the isoenzyme 3.

Still another object of the invention is to provide a reagent for use in such determinations.

Yet another object is to provide a diagnostic tool and method utilizing such reagent for use in detecting abnormal changes in the female genital tract.

In accordance with the invention, it has now been established that a lowering of the pH value to below the neutral point in carrying out the known change of lactate and NAD to pyruvate leads to an optimal detection of the total of the LDH-isoenzyme, especially however of the isoenzymes 4 and 5. Thereby it is above all of interest that only by carrying out this change in the acid pH range are the LDH 4 and 5 completely determined. Thus, the total content of all of the isoenzymes of LDH are only detected by carrying out the process for determining their presence in the acid pH range and it is hereby made possible to determine the presence of LDH 4 or 5 alone or in admixture with one another, and also with other LDH enzymes.

According to the invention, there is provided a process for the determination of at least one and including all of the isoenzymes of lactatedehydrogenase (LDH) and especially the isoenzymes 4 and 5 alone or in combination by means of the conversion of lactate and nicotinamide-adenine-dinucleotide (NAD$^+$) to pyruvate, which is characterized in that the conversion is carried out using a buffer system providing a specific value, for instance in the case of triethanolamine-NaOH buffer, a pH of 6.3–6.4. The conversion can be carried out using only a very small amount of fluid, it is advantageous however that it be carried out in some fluid.

It has furthermore been established that the optimum for the determination of the total isoenzyme content is also buffer dependent. For most of the buffers, this optimum lies at about a pH of 6–6.5. If a phosphate buffer is used, it is to be sure still possible to measure the isoenzyme content, however, there is determined thereby only a part of the total as for instance, the isoenzyme 5 can be measured at a pH of 7.9. An acid pH value is however essential for the determination of the other isoenzymes and especially for determining the total of the isoenzymes. A pH of about 6.3–6.4 has been found to be especially suitable for the combined determination of LDH 4 and 5, which for instance are to be found in the vaginal fluid.

Preferably there is provided a large buffer capacity in the medium where the conversion is to be effected. This has the advantage that also in the testing of body fluids having pH values markedly deviating from a pH of 6.0., the optimal pH for the conversion is not exceeded nor does it drop too low.

The conversion takes place in the known manner at a temperature of about 37° C. In this connection, the coenzyme is employed so that it is present in an optimally sufficient amount for determining all of the isoenzymes which are under consideration. The amount of coenzyme, etc. can be readily determined with only a little routine experimentation.

The determination of LDH is of great importance and especially its presence in body fluids. While these enzymes are in the case of healthy people preponderantly retained in tissue, it has been found that in the presence of abnormal tissue growth, leukemia and similar conditions, there is present LDH in appreciable concentration in the serum and other body fluids. It is of greatest importance that the determination of LDH can help establish that there are pathological changes in the lower female genital tract and namely the presence of LDH in the vaginal fluid is indicative of just such conditions.

The method of the invention is applicable to all body fluids. The adjustment of the pH value for the test sample depends on the characteristic pH value of that type of sample material. In each case, there is required for the conversion to take place that there be present a pH of 6.3–6.4, especially about pH 6.3. Therefore the composition of the reagent used for carrying out the determination has to be adjusted accordingly.

While by the standard method (see Enzymatic Analysis, supra), a pH optimum between 8.3 and 8.9 has heretofore been prescribed, it has now been found in accordance with the invention that this pH range is to be deviated from. The basis for the placing of the pH in this range is to be seen from the following reaction:

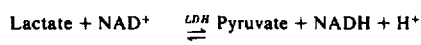

Lactate + NAD$^+$ $\underset{\rightleftharpoons}{\overset{LDH}{}}$ Pyruvate + NADH + H$^+$ A proton stands in stoichiometric relationship to the lactate conversion. In this equilibrium, in order to drive the reaction to the right, the reaction has been carried out in the alkaline range.

According to the invention, for instance in carrying out the determination is serum or plasma, the test sample is buffered with triethanolamine-NaOH to about a pH of 6.3–6.4 and also for the test, there is used a test reagent which has been adjusted to this value. Roughly stated, for the determination to be carried out, a pH value of 6.0–6.5 is to be established and it is thereby buffered so that in the determination, a pH value of 6.3–6.4 is present. With serum albumin, glutathione can be introduced in the known manner.

The isoenzymes of lactate dehydrogenase are optimally determined at a pH of 6.3–6.4. When care is taken that the reaction proceeds at this range, the reaction equilibrium is the following:

Lactate + NAD$^+$ $\underset{\rightleftarrows}{\text{LDH}}$ Pyruvate + NADH + H$^+$ and that it is maintained throughout the reaction, it will proceed to the right with the conversion being efficiently effected. This objective can be assured by adding to the reaction phenazinemethosulfate, whereby the coenzyme NADH is always further oxidized. The determination at a pH of 6.0–6.5 provides first an indication of the possibility of determining the entire LDH. This is above all important because the presence of LDH 5 is an indication of the presence of cancer and thereby there is provided an exact and sensitive means for determining the presence and that an early stage of cancer.

In certain body fluids, however, the above-described relationship will differ because the body fluids are characterized by a pH value diverging or deviating from the range of 6.3–6.4 and which are characteristic of the special fluid. Such a body fluid is for instance vaginal fluid, the pH value of which lies at about 4. In this case, one must use a test reagent which will establish the optimal pH value for the conversion which means that the test reagent must have a higher pH value so that thereby the pH value of the vaginal fluid will be adjusted to about a pH of 6–6.5.

The invention in accordance with another embodiment thereof provides a test reagent comprised of lactate, nicotinamide-adenine-dinucleotide (NAD$^+$) and a tetrazolium salt, the latter for rendering visible the enzymatic NAD$^+$ reaction, which is so buffered that a proper change in the body fluid being tested is provided, i.e. so that a buffer specific value of 6.3–6.4 is established, for instance by triethanolamine-NaOH buffer or other acid adjustable buffer with the exception of a phosphate buffer. If a dry preparation (test reagent) is used, this pH must be present on dissolution, i.e. a pH on the order of 6.0–6.5 is required to be established in the fluid medium.

In the special case where the testing of vaginal fluid is to be carried out, the original pH value thereof is changed by means of the buffer system, for instance, triethanolamine-NaOH. The test combination is adjusted to a pH of about 7.0 whereby there is brought about a pH of 6.3–6.4 in the test sample.

The invention is further concerned with the use of the method for effecting the determination and the reagents for the special application of testing for LDH in vaginal fluid, the test to be carried out in situ, i.e. in the vagina, utilizing therefor an especially designed device and thereby permitting the establishment of any possible pathological changes in the lower female genital tract. In accordance with the invention, this is achieved by applying onto a suitable carrier, as for instance a tampon, but also for instance, a test strip or foil, and through the insertion of this test device into the vagina, the reaction proceeding in the vagina on the basis of the LDH isoenzymes present in the vaginal fluid at a pH of about 6.0–6.5 and especially at a pH of 6.3–6.4.

The test reagent is composed of a test solution having one of the following compositions:

|  | Preferable test Charge | Lower and Upper Limit Range |
|---|---|---|
| Triethanolamine-NaOH-buffer pH 7.0 | 5.0mM | 1.0–150mM |
| Na lactate (sodium salt of D,L-lactic acid | 67.5mM | 20–350mM |
| Phenazinemethosulfate (PMS) | 0.1mM | 0.01mM |
| Nicotinamide-adenine-dinucleotide (NAD$^+$) | 1.5mM | 0.1–10mM |
| Nitro-blue-tetrazolium chloride (NBT) | 0.3mM | 0.01–1.5mM |

The test reatent is lightly deposited upon a suitable carrier, for instance a tampon, and the resulting treated carrier stored until ready for use.

The presence of LDH in the vaginal fluid is thereby indicated that after 5–10 minutes in the vagina, the tampon takes on a blue color. It results from the following reaction courses:
1. Lactate + NAD$^+$ $\underset{\rightleftarrows}{\text{LDH}}$ Pyruvate + NADH + H$^+$
2. NADH + Phenazinemethosulfate + H$^+$ → NAD$^+$ and reduced phenazinemethosulfate
3. Reduced phenazinemethosulfate + nitro-blue-tetrazolium chloride → formazane and phenazinemethosulfate The second and also the third reactions are tied to the lactate conversion in that the formed reduced coenzyme is likewise removed, so that in the first reaction, the equilibrium of the lactate conversion is even further displaced towards the right. This is accomplished by buffering the test charge to a pH of 7.0 before it is applied onto the tampon, the actual conversion taking place at a pH of about 6.0, especially 6.3–6.4 due to the pH of the body fluid. Thereby the isoenzymes and especially the LDH 4 and LDH 5, which in the presence of abnormal changes in the genital tract are present in the vaginal fluid can be optimally detected.

For the test reagents which are used directly in the vagina, a buffer is selected which is stable and also physiologically acceptable. An instance of a particularly good buffer in this case is triethanolamine-NaOH buffer.

The test reagents can be applied onto the carrier to be used, as for instance, the tampon in any of a number of ways, the tampon with the test reagent lightly applied thereto must be protected by application of a covering and then can be stored for long periods if kept under conditions where access to light is prevented. There are two advantageous methods for applying the test reagent to a tampon. These include an injection of about 2 ml of the preferred test reagent directly into the tampon or the impregnating of a tampon end in a length of about three-fourths cm, also with about 2 ml of test reagent and thereafter drying and especially freeze drying the tampons. The test reagent can however also be applied onto a string, tape, ribbon, foil or the like which is combined with the tampon and which later after use can be easily removed, i.e. separated from the tampon. Excellent results have also been achieved by the deposition of the test reagent onto a band, ribbon, tape, for instance of a cotton product which is then used in combination with or in place of a tampon.

The ability to carry out a rapid determination of the presence of a pathological change in the lower female geinital tract by inserting directly into the vagina the testing device has not hitherto been known. The variabilities with respect to how much vaginal fluid is available, (the amount varying from case to case) and also the fluctuations in the pH value of the vaginal fluid has to be provided for. This requires that a large buffering capacity be provided for the test reagent as only then can the determination take place in situ at a pH value of 6–6.5, especially 6.3–6.4. If it is not possible in the case of the string, ribbon, tape, etc. to provide the required buffer capacity, then the practice in such a case is to provide a larger amount of buffer on the tampon so that a sufficient amount of buffering is assured.

In such a way, there is with this test reagent provided on a carrier, advantageously made possible that a doctor need not be present, but that each woman can carry out the test on herself. The appearance of a blue coloration after 15–30 minutes on the tampon indicates the danger of a pathological change and is a warning signal for her to go see a doctor.

Where, however, the used tampon, tape, foil, ribbon, etc. is to be preserved, especially as could be the case where the use is by a doctor or if the patient wishes to send the tampon, etc. to a doctor, then an aftertreatment is to be carried out. This is to ensure that any odor is removed, that the tampon is disinfected and that the color is preserved and that for a long period of time. It has further been found that this aftertreatment is most advantageously carried out by dipping or immersing the tampon in a 20% paraloid solution (paraloid manufactured by Merck is dissolved in toluene to form a 20% solution).

Whereas until now known methods for determining LDH are definitely so-called laboratory methods, the teachings of the invention avoid the disadvantages of such methods and provide the possibility of a quick satisfactory quantitative determination and for certain application as for instance in vaginal fluids, the user himself can be the subject being tested. This is especially important in the case of new growth or tumor. In a larger number of tumor patients according to the literature heretofore about 26 enzymes have to be investigated in making a diagnosis. LDH occupies the position of highest diagnostic sensitivity. An increase of 40–90% has been found in serum in pathological conditions. In an established or proved tumor, the serial determination of LDH in serum over the course of treatment serves as a means to regulate therapy. The increase of LDH is truly in no way tumor specific. It remains but always as an indication of a serious illness and is in combination with other criteria and characteristics used to support the suspected diagnosis of a tumor.

The foregoing described test reagents applied onto tampons were utilized in a series of experiments carried out in about 100 healthy women and in patients with carcinoma colliuteri, carcinoma corporis and carcinoma in situ. The best results were obtained when the tampon was inserted for 15–30 minutes. After removal, the following range of colorations can be directly observed:

| | |
|---|---|
| No coloration | negative |
| Pink coloration | still negative |
| Light blue with violet cast | + |
| Blue | ++ |
| Dark blue | +++ |

In the case of a bluie (++) or a dark blue (+++) coloration, there proved in all cases to be a cancer, that is there was agreement with the pathological changes. With a dark blue coloring, there can nearly, without exception, be made the diagnosis of a "transformation zone," i.e. malignancy. A pink coloration was only to date found in healthy women and also in pregnant women up to the 15th day.

The process for the determination in vitro and also, for instance, in the testing of serum or plasma is carried out in the known manner. The only required change is the adjustment of a buffer specific value, for instance of 6–6.5 as compared to the heretofore used strongly basic pH value so that here a further description is not necessary. For an absolute determination, there can be a gaging or evaluation of the color by comparing the same with a standard LDH sample. The calibration sample can be preserved as has been set out above for preserving the tampon, film, ribbon, etc.

The following examples illustrate two of the possibilities of applying the test reagents onto tampons.

a. Immersion Method

The usual hygiene tampons, for instance, "o.b." made by the firm of Dr. Carl Hahn had a 1 cm wide ribbon or strip applied over the mid portion thereof so as to resemble a belt by the winding of the ribbon 1 to 2 times thereon. The covering of the tampon was removed from the opposite end portion of the tampon from that which carries the string serving as the removal aid so that the cylinder surface of the tampon is exposed. A commercial reagent glass tube having a volume of 18 ml (DIN format — Schott, Mainz) has the bottom tip portion cut off. The tampon is inserted into the thusly altered tube. The withdrawal string is fastened onto the other end of the tube with an adhesive plaster. The open side of the tube (exposed tampon end) is immersed in a solution as described under 1 above. Per tampon 2.0 ml are absorbed. The depositing of the solution and all of the here described manipulations in connection with the test reagent are carried out in a dark room, using monochromatic light (photo lamp) i.e., in the red range, red light.

The, in this way prepared tampons together with the glass tube are then still in darkness subjected to freeze drying. The tubes are removed from the tampons and still in darkness the tampons are covered over with colored paper, packet and stored so that light is not accessible to the tampons.

b. Injection method

The following procedures were carried out in the darkness (supra) with the help of a 2 ml syringe, 2 ml of the test reagent solution as described under 1 above were injected into the tampon. On the reverse side of the tampon, i.e. on the side where the withdrawal string is found, the injection needle is inserted through the cover into the tampon and moved therein in a longitudinal direction until the needle has traversed in a longitudinal direction the entire length of the tampon. Thereby it is assured that the tampon is uniformly impregnated. The tampons are then freeze dried as aforedescribed, packed and stored.

The reagent mixtures can basically be applied onto any material having an absorption capacity. For use in the determination of the isoenzymes in vaginal fluid or in the vagina, there have advantageously been used transparent foils such as cellulose acetate foils which are of the type used for electrophoresis or the product "Parafilm M" made by the American Chem. Company. In the place on the foils where LDH has been deposited, there is to be found a coloration in the blue range. These types of foils have the advantage that they are mechanically stronger than, for example, filter paper and for stabilizing and/or storage can be made completely transparent. Then all that remains on the foil is the color, its intensity substantially unchanged.

A transparency rendering bath for the cellulose foils can be selected from the following:

a. Methanol: glacial acetic acid in a ratio 85:15
b. Isobutanol: dioxan in a ratio of 1:1–3:7
c. Methylethylketone: dioxan in a ratio 3:2
d. Glacial acetic acid: dioxan in a ratio 3:2
e. Methanol: glacial acetic acid: gylcerin in a ratio 87:12:1

For the parafilm foils, it is expedient to dip them for a short period of time into 7.5% glacial acetic acid.

There can be a pretreatment with oil. Hereby there are suitably used Whitemore oil — 120 or Ondino oil-17 (Shell).

A professional doctor can apply these foils having a surface of 1.5–2.0cm$^2$ with a coloscopic action onto a mucous membrane where a change is suspected, for instance, in the vagina. In such a case if there are cell accumulations to be found which are derived from a tumor, there is observed at the point of contact with the foil, a coloration analogous to that described for the tampon use.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. Process for the determination of at least one of the isoenzymes 4 and 5 of lactate dehydrogenase in a test sample by visually observing the conversion of lactate and nicotinamideadenine-dinucleotide to pyruvate as brought about by the isoenzymes 4 and 5 of lactate dehydrogenase in a test reagent carrier which has had applied thereon said lactate and nicotinamide-adenine-dinucleotide into contact with a test sample to be assayed for said isoenzymes, said test reagent having been buffered to provide for said conversion a buffer specific pH value of 6–6.5.

2. Process according to claim 1 wherein said conversion is carried out in a liquid medium.

3. Process according to claim 1 wherein said determination is carried out in a triethanolamine-NaOH buffer system at a pH of 6–6.5.

4. Process according to claim 1 wherein the presence of said isoenzymes in a body fluid is determined and said body fluid and also the test reagent being employed are both buffered to provide a pH of 6.3–6.4 for the conversion.

5. Process according to claim 4 which comprises using a test reagent whose pH value is so buffered that it is effective in determining the isoenzyme content in a body fluid having a varying pH wherein said isoenzyme content is determined by observing the conversion of lactate and nicotinamideadenine-dinucleotide to pyruvate which occurs in said fluid at a pH of 6–6.5.

6. Process according to claim 5 wherein the test reagent and/or the body fluid being tested are maintained at a pH value of 6.3–6.5 by the buffer capacity of the test reagent.

* * * * *